United States Patent
Toftkjaer

(10) Patent No.: US 7,041,093 B2
(45) Date of Patent: May 9, 2006

(54) LIGHT GUIDE FOR COUPLING LIGHT OUTPUT FROM A LIGHT SOURCE TO THE SKIN

(75) Inventor: Gert Toftkjaer, Nearum (DK)

(73) Assignee: Danish Dermatologic Development A/S, Horsholm (DK)

( * ) Notice: Subject to any disclaimer, the term of this patent is extended or adjusted under 35 U.S.C. 154(b) by 136 days.

(21) Appl. No.: 10/332,615

(22) PCT Filed: Jul. 10, 2001

(86) PCT No.: PCT/EP01/07926

§ 371 (c)(1),
(2), (4) Date: Mar. 31, 2003

(87) PCT Pub. No.: WO02/03876

PCT Pub. Date: Jan. 17, 2002

(65) Prior Publication Data
US 2003/0163174 A1 Aug. 28, 2003

(30) Foreign Application Priority Data
Jul. 11, 2000 (GB) .................................. 0017051.4

(51) Int. Cl.
*A61B 18/18* (2006.01)
(52) U.S. Cl. .................. 606/9; 606/3; 606/16; 606/23; 607/88
(58) Field of Classification Search ............... 606/3, 606/7–10, 13, 16, 20, 22, 23, 76; 607/88–91
See application file for complete search history.

(56) References Cited

U.S. PATENT DOCUMENTS

| 4,321,930 A | * | 3/1982 | Jobsis et al. ............... 600/344 |
| 5,620,478 A | * | 4/1997 | Eckhouse ................... 607/88 |
| 2002/0183809 A1 | * | 12/2002 | Oron et al. .................. 607/88 |

FOREIGN PATENT DOCUMENTS

EP 0 885 629 A2 12/1998

* cited by examiner

*Primary Examiner*—A. Farah
(74) *Attorney, Agent, or Firm*—Pillsbury Winthrop Shaw Pittman LLP

(57) ABSTRACT

An Intense Pulsed Light apparatus for cosmetic or therapeutic treatment of the skin having a light source is provided with a light guide having an entry face in a rigid light guide component and an exit face in a flexible light guide component adapted to conform to highly curved parts of the body of a patient.

20 Claims, 2 Drawing Sheets

LIGHT GUIDE FOR COUPLING LIGHT OUTPUT FROM A LIGHT SOURCE TO THE SKIN

This application is the National Phase of International Application PCT/EP01/07926 filed 10 Jul. 2001 which designated the U.S. and that International Application was published under PCT Article 21(2) in English. This application also claims priority to Great Britain Application No. GB 0017051.4 filed 11 Jul. 2000, which document is herein incorporated by reference.

BACKGROUND OF THE INVENTION

1. Field of the Invention

The present invention relates to an improved light guide for coupling light output from a light source to the skin, especially to relatively steeply curved areas of the skin. Light guides are described which are suitable for use in cosmetic or therapeutic light treatment apparatus.

2. Description of the Related Art

Apparatus for such use will have a light source capable of a light output sufficient to produce the desired effect when properly directed to the skin of the patient. The light source is typically either a laser or a high intensity flash or continuous source of non-coherent light. In most laser systems the light is directed to the skin by transmission through air without the use of a light guide. In most non-coherent light operated systems (also known as Intense Pulsed Light or IPL System) however, and in some laser systems, the light is transmitted to the skin via a solid light guide which has a light-entry face adjacent the light source and a light exit face which contacts the skin.

Light guides of various shapes are shown in EP-A-0885629, DE-A-3803763, and U.S. Pat. No. 5,620,478. For optical transmission, and skin cooling, it has been proposed to put a gel between the light guide and the skin. Typically, the light guide is a short block of transparent, rigid, solid material which has a flat or curved skin contacting face. Materials used include glass, sapphire, and plastics. One of the advantages of non-coherent light operated systems over laser systems is that it is possible to obtain a suitable light energy flux over a larger area. This reduces treatment time and makes it easier to achieve a uniform light exposure over a large area. However, we have found that whilst the existing rigid light guides are satisfactory in use on relatively 'flat' areas of skin, they are less satisfactory when treatment is aimed at relatively highly curved areas of the body, such as the face. The difficulty in treating the face is made more severe by the skin being curved in more than one direction and by the underlying bone structure which prevents the skin being flattened by application of pressure via the light guide.

Failure of good contact between the light guide and areas of the skin can lead to untreated areas or possibly to small burns. The latter appear to result from the light energy which should penetrate down through the skin instead being absorbed in the skin surface layers. Possibly this is due to light rays impinging on the skin at a low angle of incidence.

SUMMARY OF THE INVENTION

The present invention now provides light guide for guiding light from a light generating apparatus to the skin of a patient, said light guide having a light-entry face and a light-exit face, and said light-exit face being deformable to conform its shape to the skin.

The light guide may be designed as an attachment for a pre-existing design of IPL apparatus. Especially one as described in EP 0885629.

Preferably, the light guide incorporates a material which absorbs light with wavelengths greater than 950 nm or from 750 nm for some applications e.g. skin rejuvenation treatment of vascular lesions, wrinkle removal or acne treatment. Generally, wavelengths in the range of 750 to 950 nm are relatively inefficient in such uses but have some effect and may be useful if the power available from the light source in the wavelengths up to 750 nm is not sufficient.

Preferably also, the light guide incorporates a material which transmits light within the wavelength range between 400 nm and 750 nm or from 400 nm to 950 nm absorbing no more than 10 percent of the energy of wavelengths within the respective range.

Particularly for use with a substantially monochromatic light source such as a laser, the light guide may be such as to transmit the light emitted by the light source whilst absorbing no more than 10% of its energy. The combination of a laser light source with a transmissive, low attenuation, flexible light guide provides increased efficiency of coupling of the laser light into the skin and allows blood to be pressed away from the treatment site. This reduces the amount of light energy which is lost by absorbance by the blood. The wavelength of the light source may be chosen to be appropriate for the selected treatment.

One option within the invention is that said light-exit face bounds a fluid filled chamber. Said fluid may be a gel. Preferably then, said fluid is a material having the light absorption and/or transmission properties given above.

Such a light guide preferably comprises an inlet for said fluid and an outlet for said fluid, whereby in use said fluid may be circulated through the chamber to allow for cooling of the fluid outside of the chamber. The cooled fluid may then serve to cool the skin to which the apparatus is applied in use.

Alternatively, said light-exit face may bound a body of deformable solid material.

Preferably, the light guide, especially the flexible components of the light guide (fluid containing envelope, gel or fluid contained therein and/or flexible solid material), is or are such as to absorb at least 50%, more preferably more e.g. 90% of the light having wavelengths above 950 nm, more preferably at least 90% of the light having wavelengths above 750 nm.

There is further provided apparatus for producing light pulses for application to the skin, said apparatus comprising a light source, which preferably is adapted to produce pulses of light, and a light guide positioned to receive light from the light source and to transmit the light to the skin of a patient, wherein said light guide is a light guide according to the invention as described above.

Preferably, the light source and said light guide are adapted to produce and transmit to the skin light pulses of an intensity sufficient to produce a cosmetic or therapeutic effect selected from the group consisting of depilation, coagulation of small blood vessels, increased production of skin collagen, skin rejuvenation, photodynamic therapy, tattoo removal and the treatment of acne, psoriasis, warts, vascular trauma, skin cancer, telangiectasis, capillary hemangioma, port wine stains or birthmarks, other vascular or pigmentation malformations in the skin. Such apparatus may thus be used for the treatment of wrinkles or sun damage. effects in the skin and uneven pigmentation.

Preferably the apparatus is adapted to produce a light output energy on the skin of up to 30 $J/cm^2$, e.g. from 3 to 26 J/cm², or 25 J/cm² or more. Alternatively, or additionally, the apparatus may be adapted to produce an output energy on the skin of from 3 to 10, e.g. 5 to 7 J/cm², especially for collagen remodelling.

BRIEF DESCRIPTION OF THE DRAWINGS

The invention will be further described and illustrated with reference to the embodiments shown in the accompanying drawings in which.

DETAILED DESCRIPTION

Figure 1:
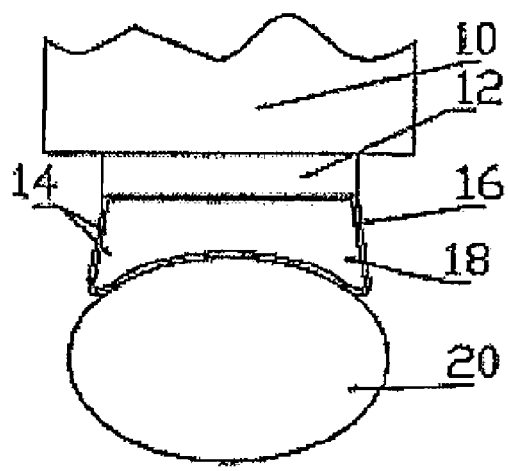
FIG. 1 is a schematic side view of a first apparatus according to the invention.

As shown in. FIG. 1, a first embodiment according to the invention comprises a light source 10, which may be a laser or non-coherent light source such as a flash lamp. Light from the light source 10 is emitted into a rigid light guide 12, which may be of glass or any material known in the art for this purpose.

Light transmitted through the rigid light guide 12 enters a flexible light guide 14 comprising a flexible outer envelope 16 containing a water based gel or demineralised water 18 or else being a unitary construction and made from a flexible light transmitting material. Examples of suitable materials include silicone rubber. The water based gel or water or the said flexible material may if desired be coloured by the inclusion of a suitable dye to filter out undesired wavelengths of light.

The light guide 14 is shown being applied to a schematically illustrated highly curved part of the body 20 against which it at least approximately conforms.

Figure 2:
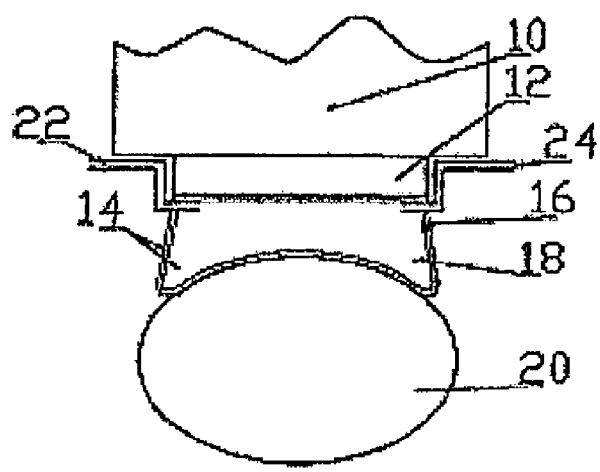
FIG. 2 is a schematic side view of a second apparatus according to the invention.

In FIG. 2, an alternative embodiment is shown in which the gel 18 is omitted. Inlet conduit 22 and outlet conduit 24 which enter and leave the envelope 16 are used to pass a cooling liquid such as water through the interior space of said envelope to a cooling station from which the liquid is recirculated to the envelope 16.

In each case, the rigid light guide 12 with the deformable light guide 14, or the deformable light guide 14 taken alone, constitutes a light guide according to the first aspect of the invention.

The materials used for the flexible light guide 14 may be chosen to be sufficiently stiff to ensure a reasonably well defined light output area but sufficiently soft and flexible to conform well with the target area. The side walls of the flexible light guide may be made more stiff than the light exit face.

Figure 3:
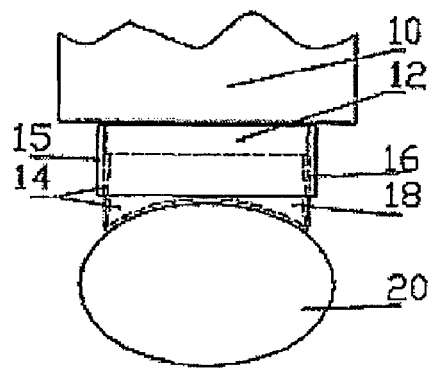
FIG. 3 is a schematic side view of a third apparatus according to the invention.
Figure 4:
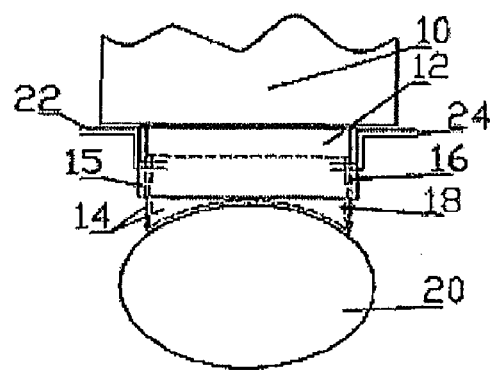
FIG. 4 is a schematic side view of a fourth apparatus according to the invention.

FIGS. 3 and 4 show modified versions of FIGS. 1 and 2 respectively in which the sides of the flexible light guide 14 are supported by a rigid tube 15, which may be of material which is reflective on its inner face such as mirror polished metal (e.g. Al) or plastics such as SPECTRALON™. This is especially desirable where the material 18 filling the envelope 16 is of low viscosity, e.g. when it is water.

The envelope 16. may be of plastics material or rubber latex. Preferably, it has a low optical attenuation. PVDF (polyvinylidene fluoride) has been found suitable as is absorbs only 1.6% of the light when used in a suitable thickness to provide the required structural integrity.

The embodiments described are especially useful in treating the highly curved areas of the face and neck in wrinkle removal and skin rejuvenation.

The invention claimed is:

1. A light guide for guiding light from a light generating apparatus to the skin of a patient, said light guide having a light-entry face and a light-exit face, and said light-exit face being deformable to conform its shape to the skin, wherein between the light-entry face and the light-exit face said light guide comprises a material which attenuates light with wavelengths greater than 950 nm.

2. A light guide as claimed in claim 1, which attenuates light with wavelengths greater than 750 nm.

3. A light guide as claimed in claim 1, which transmits light within the wavelength range of 400 to 950 nm absorbing no more than 10 percent thereof.

4. A light guide as claimed in claim 3, which transmits light within the wavelength range of 400 to 750 nm, absorbing no more than 10% thereof.

5. A light guide as claimed in claim 1, which transmits light at a wavelength appropriate for at least one cosmetic or therapeutic treatment absorbing no more than 10% of said light.

6. A light guide as claimed in claim 1, wherein said light-exit face bounds a body of deformable solid material.

7. A light guide for guiding light from a light generating apparatus to the skin of a patient, said light guide having a light-entry face and a light-exit face, and said light-exit face being deformable to conform its shape to the skin, wherein said light-exit face bounds a fluid filled chamber.

8. A light guide as claimed in claim 7, comprising an inlet for said fluid and an outlet for said fluid, whereby in use said fluid may be circulated through the chamber so as to allow cooling of the fluid outside of the chamber.

9. A light guide as claimed in claim 8, wherein said fluid is water.

10. Apparatus for cosmetic or therapeutic intense pulsed light (IPL) treatment, said apparatus comprising a light source and a light guide positioned to receive light from the light source and to transmit the light to the skin of a patient to produce cosmetic or therapeutic changes therein, wherein said light guide has a light-entry face and a light-exit face, and said light-exit face is deformable to conform its shape to the skin, wherein said light guide light exit face bounds a fluid filled chamber, further comprising a cooling unit connected in a flow circuit with said fluid filled chamber via an inlet and an outlet, for cooling said fluid.

11. Apparatus as claimed in claim 10, wherein the light source and said light guide are adapted to produce and transmit to the skin light pulses of an intensity sufficient to produce a cosmetic or therapeutic effect selected from the group consisting of depilation, coagulation of small blood vessels, increased production of skin collagen, skin rejuvenation, photodynamic therapy, tattoo removal and the treatment of psoriasis, vascular trauma, telangiectasis, capillary hemangioma, cancerous cells, port wine stains or birthmarks.

12. Apparatus as claimed in claim 10, adapted to produce a light output energy density on the skin of 25 J/cm² or more.

13. Apparatus as claimed in claim 10, adapted to produce a light output energy density on the skin of up to 30 J/cm².

14. Apparatus as claimed in claim 13, adapted to produce a light output energy density on the skin of from 3 to 26 J/cm².

15. Apparatus as claimed in claim 10, wherein said light source is a monochromatic light source and said light guide transmits light at the wavelength of the light source absorbing no more than 10% of said light.

16. Apparatus as claimed in claim 15, wherein said light source is a laser.

17. Apparatus for cosmetic or therapeutic intense pulsed light (IPL) treatment, said apparatus comprising a light source and a light guide positioned to receive light from the light source and to transmit the light to the skin of a patient to produce cosmetic or therapeutic changes therein, wherein said light guide has a light-entry face and a light-exit face, and said light-exit face is derivable to conform its shape to the skin, wherein between the light-entry face and the light-exit face said light guide comprises a material which attenuates light with wavelengths greater than 950 nm.

18. Apparatus for cosmetic or therapeutic intense pulsed light (IPL) treatment, said apparatus comprising a light source and a light guide positioned to receive light from the light source and to transmit the light to the skin of a patient to produce cosmetic or therapeutic changes therein, wherein said light guide has a light-entry face and a light-exit face, and said light-exit face is deformable to conform its shape to the skin, wherein between the light-entry face and the light-exit face said light guide comprises a material which attenuates light with wavelengths greater than 750 nm.

19. Apparatus as claimed in claim 17, wherein said light guide transmits light within the wavelength range of 400 to 950 nm absorbing no more than 10 percent thereof.

20. Apparatus as claimed in claim 17, wherein said light guide transmits light within the wavelength range of 400 to 750 nm absorbing no more than 10 percent thereof.

* * * * *